US00PP23157P3

(12) United States Plant Patent
Klemm et al.

(10) Patent No.: US PP23,157 P3
(45) Date of Patent: Oct. 30, 2012

(54) ***PETUNIA* PLANT NAMED 'KLEPH10184'**

(50) Latin Name: *Petunia hybrida*
Varietal Denomination: KLEPH10184

(75) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 29 days.

(21) Appl. No.: 13/065,821

(22) Filed: Mar. 29, 2011

(65) Prior Publication Data

US 2012/0255080 P1 Oct. 4, 2012

(51) Int. Cl.
*A01H 5/00* (2006.01)

(52) U.S. Cl. ..... Plt./356.12

(58) Field of Classification Search ..... Plt./356.1, Plt./356.12
See application file for complete search history.

*Primary Examiner* — Susan McCormick Ewoldt
(74) *Attorney, Agent, or Firm* — Jondle & Associates, P.C.

(57) ABSTRACT

A new variety of *Petunia* named 'KLEPH10184' particularly characterized by its double, white flowers, and a compact and semi trailing growth habit, is disclosed.

1 Drawing Sheet

Genus and species: *Petunia hybrida.*
Variety denomination: 'KLEPH10184'.

BACKGROUND OF THE NEW PLANT

The present invention comprises a new and distinct variety of *Petunia*, botanically known as *Petunia hybrida*, and hereinafter referred to by the variety name 'KLEPH10184'. 'KLEPH10184' was discovered as a seedling resulting from a cross conducted in the Summer of 2006 in Stuttgart, Germany between the proprietary female *Petunia* plant, 'KLEPH07145' (U.S. Plant Pat. No. 20,119), and the proprietary male *Petunia* plant, 'Odyssey' (unpatented). A single plant selection was subsequently chosen for further evaluation and asexual propagation.

The new variety was first propagated via vegetative cuttings and invitro propagation in the Summer of 2006 in Stuttgart, Germany and has been asexually reproduced repeatedly by vegetative cuttings in Stuttgart, Germany for more than 45 generations. 'KLEPH10184' has been found to retain its distinctive characteristics through successive asexual propagations via vegetative cuttings.

Plant Breeder's Rights for this variety have not been applied for. 'KLEPH10184' has not been made publicly available more than one year prior to filing of this application.

SUMMARY OF THE INVENTION

The following are the most outstanding and distinguishing characteristics of this new variety when grown under normal horticultural practices in Stuttgart, Germany.

1. Double, white flowers; and
2. Compact and semi-trailing growth habit.

DESCRIPTION OF THE PHOTOGRAPH

This new *Petunia* plant is illustrated by the accompanying photograph which shows the plant habit including flowers, flower buds, and foliage. The colors shown are as true as can be reasonably obtained by conventional photographic procedures. The photograph was taken in May 2010 of a 5-month old plant grown from rooted cuttings in an 11 centimeter pot in a glass greenhouse in Stuttgart, Germany under normal horticultural practices.

DESCRIPTION OF THE NEW VARIETY

The following detailed descriptions set forth the distinctive characteristics of 'KLEPH10184'. The data which define these characteristics were collected from asexual reproductions carried out in Stuttgart, Germany. The plant history was taken in May 2010 on 3-month old plants grown in 11 centimeter pots in a glass greenhouse that were pinched once approximately one week after potting. The color readings were determined under natural light. Color references are to The R.H.S. Colour Chart of The Royal Horticultural Society of London (RHS), Fifth Edition (2007).

DETAILED BOTANICAL DESCRIPTION OF THE NEW PLANT

Classification:
- *Family.*—Solanaceae.
- *Genus and species.—Petunia hybrida.*
- *Common name.—Petunia.*

Parentage:
- *Female parent.*—The proprietary *Petunia* 'KLEPH07145' (U.S. Plant Pat. No. 20,119).
- *Male parent.*—The proprietary *Petunia* 'Odyssey' (unpatented).

Plant:
- *Form.*—Compact.
- *Habit.*—Semi-trailing.
- *Height (from top of soil).*—12.0 cm.
- *Width (horizontal plant diameter).*—15.0 cm.
- *Propagation.*—Terminal tip cutting and tissue culture.
- *Time to produce a finished flowering plant.*—11 weeks.
- *Time to initiate and develop roots.*—Approximately 16 days.
- *Root description.*—Moderate density and branching.
- *Root color.*—White.

Stems:

*Average number* (*basal*).—5.

*Length of basal branches* (*from the base of the stem to the tip*).—8.0 cm.

*Internode length*.—1.5 cm to 2.5 cm.

*Diameter of branches* (*from midpoint*).—0.4 cm to 1.0 cm.

*Stem color*.—RHS 144B.

*Anthocyanin*.—Absent.

*Texture*.—Smooth.

Leaves:

*Arrangement*.—Alternate.

*Size*.—Length: 3.0 cm to 5.0 cm. Width: 1.5 cm to 3.0 cm.

*Shape*.—Broad elliptic.

*Margin*.—Weak undulation.

*Apex*.—Acute.

*Base*.—Abtuse.

*Color*.—Both immature and mature leaf: Upper surface: RHS 143A. Lower surface: RHS 138B.

*Texture* (*both upper and lower surfaces*).—Smooth.

*Venation*.—Pinnate. Venation color: Upper surface: RHS 144B. Lower surface: RHS 144C.

*Petioles*.—Length: 0.2 cm to 1.0 cm. Diameter: 0.2 cm. Color: Upper surface: RHS 143A. Lower surface: RHS 138B. Texture: Smooth.

Flower bud:

*Shape*.—Irregular-oblong.

*Size*.—Length: 3.5 cm. Diameter: 2.5 cm.

*Color at tight bud*.—Light green.

*Immature flower color*.—RHS 155A.

Inflorescence:

*Blooming habit* (*flowering season*).—Permanent flowering during summertime.

*Inflorescence type*.—Double flowering.

*Number of flowers per node*.—1.

*Lastingness of individual blooms on the plant*.—7 days.

*Fragrance*.—Absent.

*Pedicels*.—Color: RHS 144A. Length: 2.0 cm. Diameter: 0.3 cm. Texture: Smooth.

Flowers:

*Shape*.—Cup-shaped.

*Size*.—Diameter (flower face): 5.5 cm. Depth (total length of flower): 5.0 cm. Funnel: Length: 2.5 cm. Diameter (at opening): 1.5 cm. Outside texture: Smooth.

*Mature flower*.—Face/Margin color (both surfaces): RHS 155A. Corolla tube: Shape: Funnel. Color inside (throat): RHS 155A. Color outside: RHS 155A. Petals: Apex: Rounded to emarginate. Base: Uniform. Margin: Undulating. Waviness: Medium. Lobation: Medium. Texture (both upper and lower surfaces): Smooth.

*Calyx arrangement*.—Actinomorphic.

*Sepals*.—Number: 5. Color: Upper surface: RHS 138A. Lower surface: RHS 138B. Length: 1.5 cm. Width: 0.4 cm. Shape: Lanceolate. Apex: Obtuse. Base: Open. Margin: Entire. Texture (both upper and lower surfaces): Smooth.

Reproductive organs:

*Stamens*.—Quantity: 5. Shape: Needle with elliptic head. Color: RHS 189D. Filament: Length: 1.2 cm. Diameter: 0.1 cm. Anther: Shape: Elliptic. Color: RHS 189D. Length: 0.2 cm. Diameter: 0.2 cm. Pollen: Color: RHS 188D. Amount: Sparse.

Fruit and seed set: None observed.

COMPARISON WITH PARENTAL AND COMMERCIAL VARIETIES

'KLEPH10184' differs from the female parent, the proprietary *Petunia* 'KLEPH07145' (U.S. Plant Pat. No. 20,119), in that 'KLEPH10184' has white flowers, while 'KLEPH07145' has lemon-yellow colored flowers.

'KLEPH10184' differs from the male parent, the proprietary *Petunia* 'Odyssey' (unpatented), in that 'KLEPH10184' has white flowers, while 'Odyssey' has pink flowers.

'KLEPH10184' differs from the commercial cultivar 'Duepotdared' (U.S. Plant Pat. No. 21,704) in that 'KLEPH10184' has double, white flowers, while 'Duepotdared' has single, red flowers.

We claim:

1. A new and distinct variety of *Petunia* plant named 'KLEPH10184' as shown and described herein.

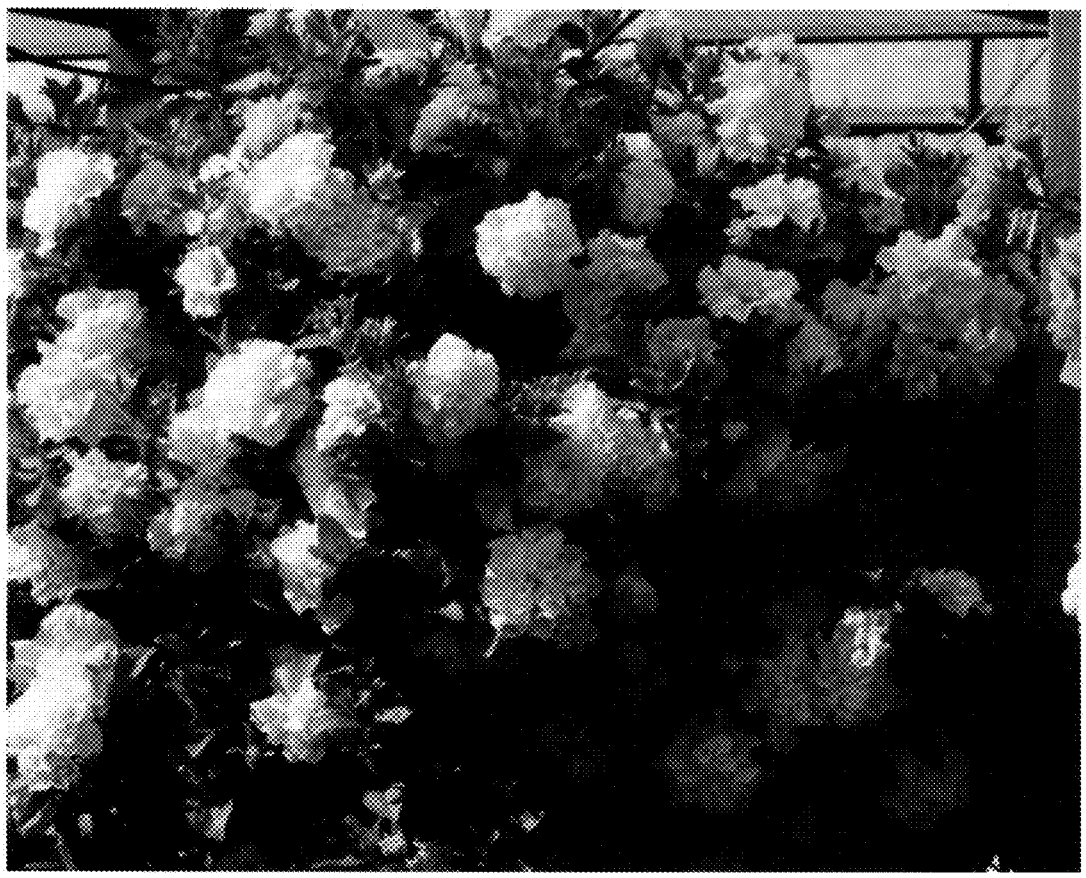

* * * * *